US00PP36572P3

(12) United States Plant Patent
Hoogkamp

(10) Patent No.: US PP36,572 P3
(45) Date of Patent: Mar. 25, 2025

(54) ***CURCUMA* PLANT NAMED 'Curalivemowiblo'**

(50) Latin Name: *Curcuma alismatifolia*
Varietal Denomination: Curalivemowiblo

(71) Applicant: NUBILUS B.V., Naaldwijk (NL)

(72) Inventor: Timothy Johan Herman Hoogkamp, Doetinchem (NL)

(73) Assignee: NUBILUS B.V., Naaldwijk (NL)

( * ) Notice: Subject to any disclaimer, the term of this patent is extended or adjusted under 35 U.S.C. 154(b) by 0 days.

(21) Appl. No.: 18/733,333

(22) Filed: Jun. 4, 2024

(65) Prior Publication Data

US 2024/0415041 P1 Dec. 12, 2024

Related U.S. Application Data

(60) Provisional application No. 63/471,458, filed on Jun. 6, 2023.

(51) Int. Cl.
*A01H 5/02* (2018.01)
*A01H 6/00* (2018.01)

(52) U.S. Cl.
USPC ..... Plt./421
CPC ..... *A01H 6/00* (2018.05)

(58) Field of Classification Search
USPC ..... Plt./421
See application file for complete search history.

*Primary Examiner* — Susan McCormick Ewoldt
(74) *Attorney, Agent, or Firm* — C. Anne Whealy

(57) ABSTRACT

A new and distinct cultivar of *Curcuma* plant named 'Curalivemowiblo', characterized by its compact and upright plant habit with outwardly arching leaves; moderately vigorous growth habit; freely clumping growth habit; medium green-colored leaves with dark reddish brown-colored midvein on the upper surface; freely flowering habit; and large dense inflorescences with white-colored upper flower bracts with medium green-colored apices positioned above the foliar plane on strong and erect peduncles.

3 Drawing Sheets

Figure 1:
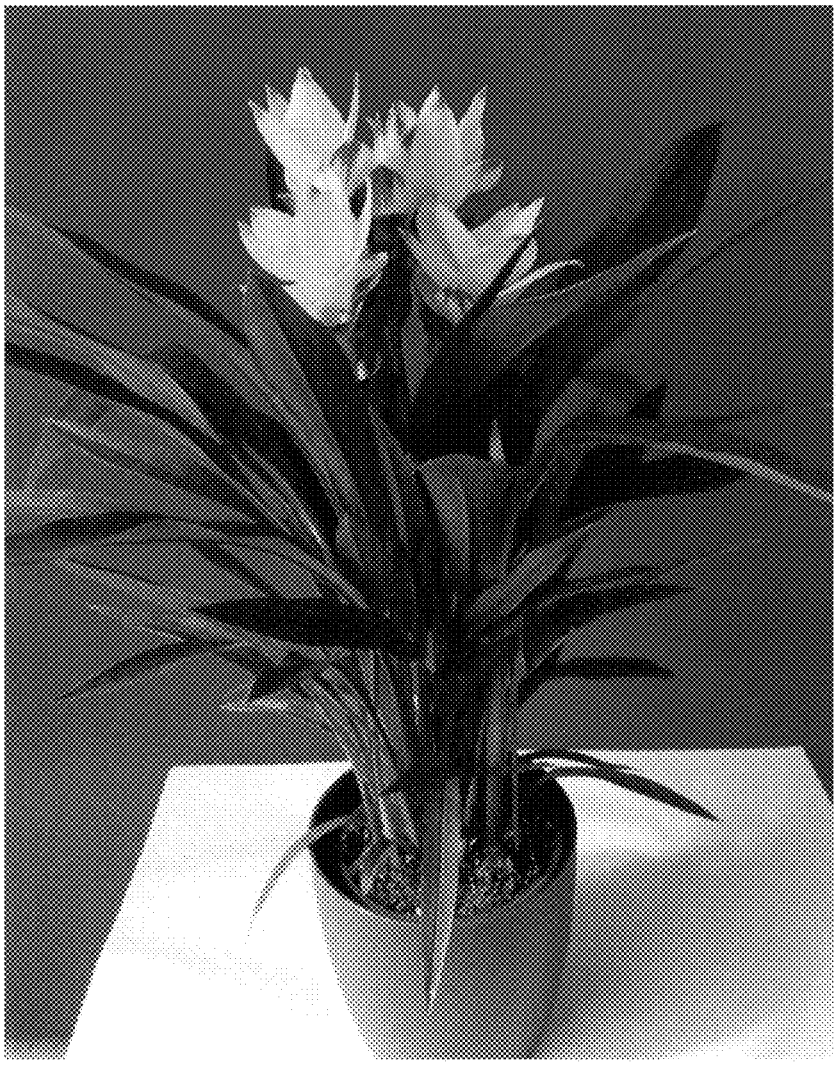

Botanical designation: *Curcuma alismatifolia.*
Cultivar denomination: 'CURALIVEMOWIBLO'.

STATEMENT REGARDING PRIOR DISCLOSURES BY INVENTOR & APPLICANT/ASSIGNEE

A European Community Plant Breeder's Rights application for the instant plant was filed by the Applicant/Assignee, Nubilus B. V. of Naaldwijk, The Netherlands on Dec. 13, 2022, application number 2022/2921. Foreign priority is not claimed to this application.

A Canadian Plant Breeder's Rights application for the instant plant was filed by the Applicant/Assignee, Nubilus B. V. of Naaldwijk, The Netherlands on Jan. 5, 2024, application number 24-11565. Foreign priority is not claimed to this application.

The Inventor/Applicant and Assignee hereby assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Curcuma* plant, botanically known as *Curcuma alismatifolia* and hereinafter referred to by the name 'Curalivemowiblo'.

The new *Curcuma* plant is a product of a controlled breeding program conducted by the Inventor in Naaldwijk, The Netherlands. The objective of the breeding program is to create new *Curcuma* plants that have uniform plant habit, good container performance and attractive inflorescence coloration.

The new *Curcuma* plant originated from a cross-pollination in May 2018 in Naaldwijk, The Netherlands of a proprietary selection of *Curcuma alismatifolia* identified as code number 20164133-02, not patented, as the female, or seed, parent with a proprietary selection of *Curcuma alismatifolia* identified as code number 20153934-002, not patented, as the male, or pollen, parent. The new *Curcuma* plant was discovered and selected by the Inventor as a single flowering plant from within the progeny of the stated cross-pollination grown in a controlled greenhouse environment in Naaldwijk, The Netherlands in July 2019.

Asexual reproduction of the new *Curcuma* plant by in vitro meristem culture in a controlled environment in Naaldwijk, The Netherlands since October 2019 has shown that the unique features of this new *Curcuma* plant are stable and reproduced true to type in successive generations.

SUMMARY OF THE INVENTION

Plants of the new *Curcuma* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Curalivemowiblo'. These characteristics in combination distinguish 'Curalivemowiblo' as a new and distinct *Curcuma* plant:

1. Compact and upright plant habit with outwardly arching leaves.
2. Moderately vigorous growth habit.
3. Freely clumping growth habit.
4. Medium green-colored leaves with dark reddish brown-colored midvein on the upper surface.
5. Freely flowering habit.
6. Large dense inflorescences with white-colored upper flower bracts with medium green-colored apices positioned above the foliar plane on strong and erect peduncles.

Plants of the new *Curcuma* differ from plants of the female parent selection in the following characteristics:

1. Plants of the new *Curcuma* are shorter and more compact than plants of the female parent selection.
2. Plants of the new *Curcuma* have white-colored upper flower bracts with medium green-colored apices whereas plants of the female parent selection have white-colored upper bracts with pink-colored apices.

Plants of the new *Curcuma* differ from plants of the male parent selection in the following characteristics:

1. Plants of the new *Curcuma* are shorter and more compact than plants of the male parent selection.
2. Plants of the new *Curcuma* have white-colored upper flower bracts with medium green-colored apices whereas plants of the male parent selection have creamy white-colored upper bracts.

Plants of the new *Curcuma* can also be compared to plants of *Curcuma alismatifolia* 'Curhalawi', disclosed in U.S. Plant Pat. No. 30,408. In side-by-side comparisons plants of the new *Curcuma* differ from plants of 'Curhalawi' in the following characteristics:

1. Plants of the new *Curcuma* are shorter and more compact than plants of 'Curhalawi'.
2. Plants of the new *Curcuma* flower about three weeks earlier than plants of 'Curhalawi'.
3. Upper flower bracts of plants of the new *Curcuma* are broader than upper flower bracts of plants of 'Curhalawi'.

BRIEF DESCRIPTION OF THE PHOTOGRAPHS

The accompanying photographs illustrate the overall appearance of the new *Curcuma* plant showing the colors as true as it is reasonably possible to obtain in colored reproductions of this type. Colors in the photographs may differ slightly from the color values cited in the detailed botanical description which accurately describe the colors of the new *Curcuma* plant.

The photograph on the first sheet (FIG. 1) is a side perspective view of a typical plant of 'Curalivemowiblo' grown in a container.

Figure 2:
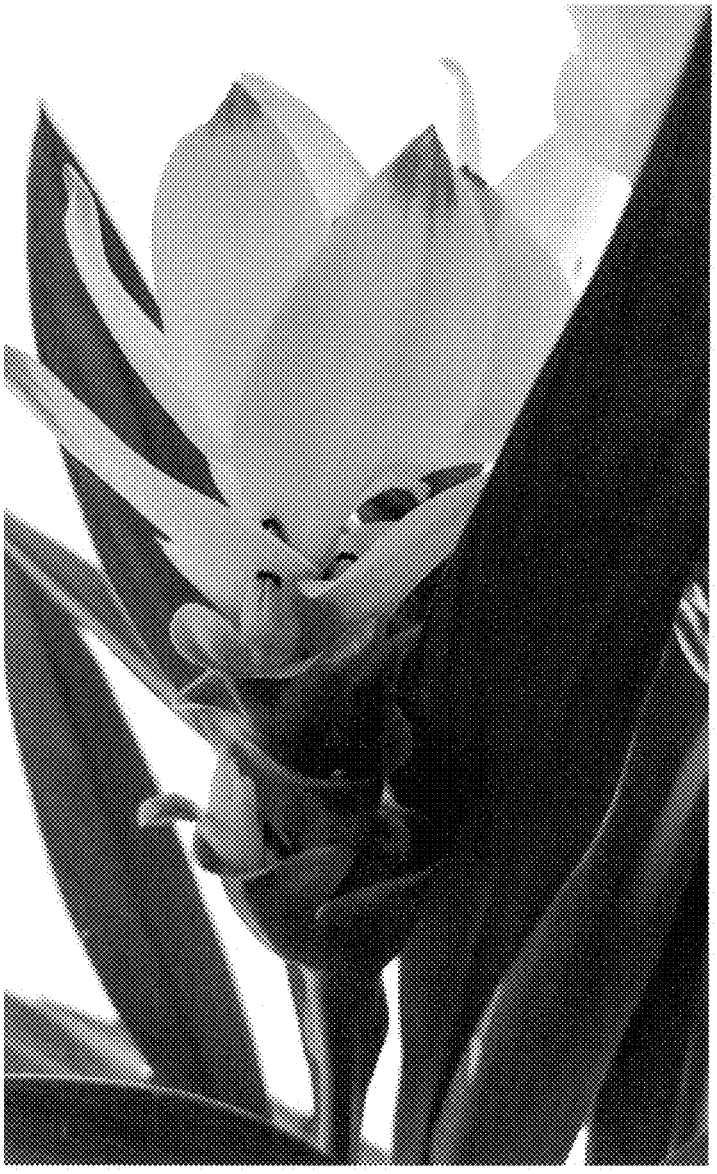

The photograph on the second sheet (FIG. 2) is a close-up view of a typical flowering plant of 'Curalivemowiblo'.

Figure 3:
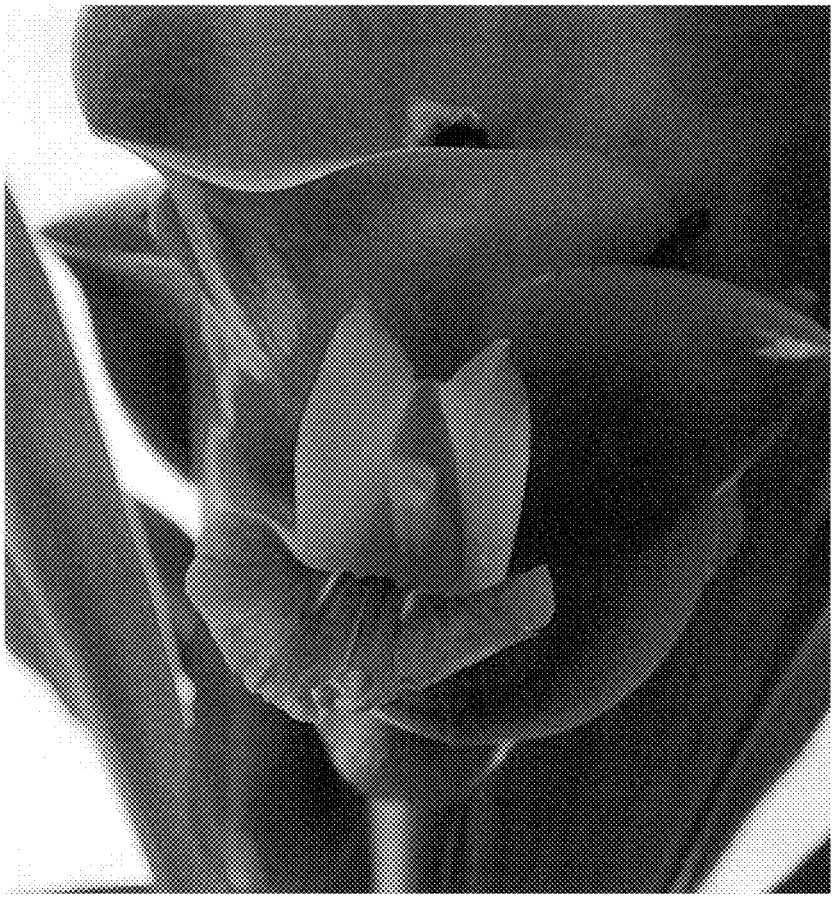

The photograph on the third sheet (FIG. 3) is a close-up view of a typical flower of 'Curalivemowiblo'.

DETAILED BOTANICAL DESCRIPTION

The aforementioned photographs and following observations and measurements describe plants grown during the winter in 14-cm containers in a glass-covered greenhouse in Naaldwijk, The Netherlands and under cultural practices typical of commercial *Curcuma* production. During the production of the plants, day temperatures ranged from 22° C. to 25° C., night temperatures ranged from 20° C. to 22° C. and light levels averaged 55 kilolux. Plants were 15 weeks old when the photographs and the detailed description were taken. In the following description, color references are made to The Royal Horticultural Society Colour Chart, 2015 Edition, except where general terms of ordinary dictionary significance are used.

Botanical classification: *Curcuma alismatifolia* 'Curalivemowiblo'.

Parentage:

*Female, or seed, parent*.—Proprietary selection of *Curcuma alismatifolia* identified as code number 20164133-02, not patented.

*Male, or pollen, parent*.—Proprietary selection of *Curcuma alismatifolia* identified as code number 20153934-002, not patented.

Propagation:

*Type*.—By axillary bud meristem culture.

*Time to initiate roots*.—About ten days at temperatures about 23° C.

*Time to produce a rooted young plant*.—About 28 to 30 days at temperatures about 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately branching, medium density.

Plant description:

*Plant and growth habit*.—Compact and upright plant habit with outwardly arching leaves; overall shape, broadly elliptic to broadly obovate; freely clumping habit with about eleven basal shoots forming per plant; moderately vigorous growth habit and moderate growth rate.

*Plant height* (*soil level to top of foliar plane*).—About 29.7 cm.

*Plant height* (*soil level to top of floral plane*).—About 37.4 cm.

*Plant diameter*.—About 46.4 cm.

Leaf description:

*Leaf arrangement*.—Alternate; simple.

*Length, fully expanded*.—About 24.7 cm.

*Width, fully expanded*.—About 4.1 cm.

*Shape*.—Narrowly elliptic.

*Apex*.—Narrowly apiculate.

*Base*.—Attenuate, sheathing.

*Margin*.—Entire; not lobed, not undulate.

*Venation*.—Parallel.

*Aspect*.—Initially upright, then outwardly arching.

*Texture and luster, upper and lower surfaces*.—Smooth, glabrous; non-rugose; matte.

*Color*.—Developing leaves, upper surface: Close to 137B. Developing leaves, lower surface: Close to a blend of 138A and 147B. Fully expanded leaves, upper surface: Close to NN137C; main vein and secondary veins, close to 200B and 200C. Fully expanded leaves, lower surface: Close to NN137D; main vein, close to NN137D and secondary veins, close to NN137B.

*Leaf sheaths*.—Length: About 10 cm. Width: About 8 mm. Texture and luster, upper surface: Smooth, glabrous; moderately glossy. Texture and luster, lower surface: Smooth, glabrous; slightly glossy. Color, upper surface: Close to 144A; marginal edges, closer to 145C and mostly translucent; venation, close to 197A. Color, lower surface: Close to 143A; marginal edges, close to 145C and mostly translucent; venation, close to N199B, 200B and 200C.

*Petioles*.—Length: About 12.8 cm. Width: About 5 mm by 5.5 mm. Strength: Strong. Texture and luster, upper and lower surfaces: Smooth, glabrous; slightly glossy. Color, upper surface: Close to 141A and 141B. Color, lower surface: Close to 137C.

Inflorescence description:

*Arrangement*.—Upright terminal spike inflorescences developing directly from the basal shoots with showy upper flower bracts; typically each spike with about eleven clusters each with about four flowers; about 132 flowers buds and flowers developing per plant during the flowering season.

*Time to flower*.—In The Netherlands, plants flower from summer into autumn; flowering continuous during this period; plants begin flowering about eleven weeks after planting.

*Flower longevity*.—Flowers last about one day on the plant; flowers persistent; plants maintain good substance and appearance for about 40 days.

*Fragrance*.—Moderate; somewhat spicy.

*Flower buds*.—Length: About 1.1 cm. Diameter: About 4.5 mm. Shape: Elliptic. Texture and luster: Smooth, glabrous; slightly glossy. Color: Proximally, close to 156D; distally, close to 85D.

*Inflorescence length*.—About 15.5 cm.

*Inflorescence diameter, with bracts*.—About 8.2 cm.

*Flowers*.—Diameter: About 1.2 cm by 1.9 cm. Depth: About 3.4 cm. Flower throat diameter: About 6 mm. Flower tube length: About 1.6 cm. Flower tube diameter: About 3 mm. Shape and arrangement: Zygomorphic with three petals, conspicuous labellum and two lateral corolla lobes (staminodia), fused towards the base; gamosepalous calyx with three sepals.

*Labellum*.—Length: About 2 cm. Width: About 1.5 cm. Shape: Obovate; fused towards the base. Apex: Emarginate. Margins: Entire; slightly undulate. Texture and luster, upper surface: Smooth, glabrous; slightly velvety; slightly glossy. Texture and luster, lower surface: Smooth, glabrous; slightly glossy. Color: When opening and fully opened, upper surface: Close to 86B fading towards the margins to close to 86D and to the base to close to N87D; central narrow stripe, close to 14B; margins, close to NN155A; venation, similar to lamina colors; color becoming closer to 77A and 77B with subsequent development. When opening and fully opened, lower surface: Close to 86D fading towards the base to close to 22B; central band, close to 85D; venation, similar to lamina colors; color becoming closer to 77C and 77D with subsequent development.

*Lateral corolla lobes* (*staminodia*).—Length: About 1.7 cm. Width: About 7 mm. Shape: Narrowly ovate. Apex: Acute. Margins: Entire; not undulate. Texture and luster, upper surface: Smooth, glabrous; matte. Texture and luster, lower surface: Smooth, glabrous; slightly glossy. Color: When opening and fully opened, upper surface: Close to NN155D fading towards the apex, close to 155C; venation, close to NN155A; colors do not change with subsequent development. When opening and fully opened, lower surface: Close to NN155D fading towards the apex, close to 155C; venation, close to NN155A; colors do not change with subsequent development.

*Petals*.—Length, dorsal and lateral petals: About 1.4 cm. Width, dorsal petal: About 1.1 cm. Width, lateral petals: About 7 mm. Shape, dorsal petal: Oblong. Shape, lateral petals: Narrowly ovate. Apex, dorsal petal: Broadly acute. Apex, lateral petals: Acute. Base, dorsal and lateral petals: Proximal 57.5% of the petal length is fused into a tube. Margins, dorsal and lateral petals: Entire; not undulate. Texture and luster, dorsal and lateral petals, upper surface: Smooth, glabrous; slightly glossy. Texture and luster, dorsal and lateral petals, lower surface: Smooth, glabrous; moderately glossy. Texture, throat and tube: Smooth, glabrous. Color, dorsal and lateral petals: When opening and fully opened, upper surface: Close to NN155D; venation, close to NN155A; color does not change with subsequent development. When opening and fully opened, lower surface: Close to NN155D; venation, close to NN155A; color does not change with subsequent development. Color, flower throat: Close to NN155C; venation, close to NN155C. Color, flower tube: Close to NN155A; venation, close to NN155A.

*Calyx*.—Length: About 9 mm. Diameter: About 5 mm. Quantity of sepals and arrangement: Three in a single whorl; fused at the base. Sepal length: About 9 mm. Sepal width: About 3.5 mm. Sepal shape: Short oblong. Sepal apex: Broadly and bluntly acute. Sepal base: Broadly cuneate. Sepal margin: Entire. Sepal texture and luster, upper and lower surfaces: Smooth, glabrous; slightly glossy. Sepal color: When opening and fully opened, upper surface: Close to NN155D. When opening and fully opened, lower surface: Close to NN155D.

*Upper flower bracts*.—Quantity: About eight to ten upper bracts per inflorescence. Length: About 6.6 cm. Width: About 4 cm. Shape: Ovate; slightly concave. Apex: Broadly acute. Base: Cuneate. Margin: Entire; slightly and coarsely undulate. Texture and luster, upper surface: Smooth, glabrous; slightly glossy. Texture and luster, lower surface: Smooth, glabrous; moderately glossy. Color: When opening and fully opened, upper surface: Close to NN155D; towards the apex, close to 145A with a blotch, close to 37C to 37D; towards the base, close to 145A and 145B; venation, similar to lamina colors; colors do not change with subsequent development. When opening and fully opened, lower surface: Close to NN155D; towards the apex, close to 146C and 146D; towards the base, close to 145A and 145B; venation, similar to lamina colors; colors do not change with subsequent development.

*Lower flower bracts*.—Quantity: About eleven lower bracts per inflorescence. Length: About 3.5 cm. Width: About 4.8 cm. Shape: Broadly flabellate; strongly concave. Apex: Broadly and shallowly retuse. Base: Cuneate. Margin: Entire; undulate. Texture and luster, upper surface: Smooth, glabrous; slightly glossy. Texture and luster, lower surface: Smooth, glabrous; glossy. Color: When opening and fully opened, upper surface: Close to 144A and towards the margins, close to 144B and 144C; venation, similar to lamina colors; colors do not change with subsequent development. When opening and fully opened, lower surface: Close to a blend of 144A and 146B; venation, close to 137A; color does not change with subsequent development.

*Peduncles*.—Length: About 29.4 cm. Diameter: About 6 mm. Strength: Strong. Aspect: Mostly erect. Texture and luster: Smooth, glabrous; matte. Color: Close to 137C.

*Stamens*.—Quantity: Three per flower; anthers fused. Filament length: About 8 mm. Filament diameter: About 5 mm. Filament color: Close to NN155D. Anther size: About 1 mm by 7 mm. Anther shape: Narrowly oblong. Anther color: Close to 155A with hood-like structure, close to 155B with apex, close to 86D. Pollen amount: Moderate. Pollen color: Close to NN155A.

*Pistils*.—Quantity per flower: One. Pistil length: About 2.8 cm. Style length: About 2 cm. Style color: Close to NN155D. Stigma diameter: About 2.5 mm. Stigma shape: Cupped. Stigma color: Close to NN155D. Ovary color: Close to 157A.

*Seeds and fruits*.—To date, seed and fruit development have not been observed on plants of the new *Curcuma*.

Pathogen & pest resistance: To date, plants of the new *Curcuma* have not been observed to be resistant to pathogens or pests common to *Curcuma* plants.

Temperature tolerance: Plants of the new *Curcuma* have been observed to be tolerant to temperatures ranging from about 5° C. to about 40° C. and are suitable for USDA Hardiness Zones 10 to 12.

It is claimed:

1. A new and distinct *Curcuma* plant named 'Curalivemowiblo' as herein illustrated and described.

* * * * *